United States Patent [19]

Temple et al.

[11] Patent Number: 4,628,089
[45] Date of Patent: Dec. 9, 1986

[54] PYRIDO(2,3-D)PYRIMIDINES

[75] Inventors: Carroll G. Temple; John A. Montgomery; Robert D. Elliott, all of Birmingham, Ala.

[73] Assignee: Southern Research Institute, Birmingham, Ala.

[21] Appl. No.: 712,116

[22] Filed: Mar. 15, 1985

Related U.S. Application Data

[60] Division of Ser. No. 673,283, Nov. 20, 1984, Pat. No. 4,536,575, which is a division of Ser. No. 413,501, Aug. 31, 1982, Pat. No. 4,526,964, which is a continuation-in-part of Ser. No. 338,542, Jan. 11, 1982, Pat. No. 4,431,805, which is a continuation-in-part of Ser. No. 305,907, Sep. 25, 1981, abandoned.

[51] Int. Cl.$^4$ ............................................ C07D 487/02
[52] U.S. Cl. ........................................ 544/244; 544/279
[58] Field of Search ............................... 544/279, 244

[56] References Cited

U.S. PATENT DOCUMENTS

| | | | |
|---|---|---|---|
| 3,021,332 | 2/1962 | Hitchings et al. | 544/279 |
| 3,288,792 | 11/1966 | Hitchings et al. | 544/279 |
| 4,431,805 | 2/1984 | Temple et al. | 544/279 |
| 4,460,591 | 7/1984 | DeGraw et al. | 544/279 |
| 4,526,964 | 7/1985 | Temple et al. | 544/279 |
| 4,532,241 | 7/1985 | DeGraw et al. | 544/279 |
| 4,536,575 | 8/1985 | Temple et al. | 544/279 |

OTHER PUBLICATIONS

Smith et al., Biochemistry, vol. 20, pp. 1241–1245, (1981).
Tseng, C. P., "Studies in Synthetic Heterocyclic Chemistry" pp. 171–185, (1979).
Mulvery et al., J. Org. Chem., vol. 29, pp. 2903–2907, (1982).
Temple et al., J. Org. Chem., vol. 47, pp. 761–765, (1982).
Piper et al., J. Org. Chem., vol. 42, No. 2, pp. 208–211, (1977).
Temple et al., "Synthesis of Potential Anticancer Agents", Report 85, pp. 1 & 2, (1966), Report 86, pp. 8 & 10, (1967).
Scanlon et al., Molecular Pharmacology, vol. 16, pp. 261–269, (1979).
Irwin et al., Advanced Heterocyclic Chemistry, vol. 10, pp. 149–171, (1969).
Bird et al., Molecular Pharmacology, vol. 6, pp. 573–575, (1970).
Trattner et al., J. Org. Chem., vol. 29, pp. 2674–2677, (1964).
Hurst, "An Introduction to the Chemistry and Biochemistry of Pyrimidines, Purines and Pteridines", p. 231, John Wiley & Sons, (1980).
Srinivasan et al., J. Org. Chem., vol. 45, pp. 3746–3748, (1980).
Bennett et al., J. Med. Chem., vol. 24, pp. 382–389, (1981).
Robins et al, J. Am. Chem. Soc., vol. 77, pp. 2256–2260, (1955).
Calvert et al., European J. Cancer, vol. 16, pp. 713–722, (1980).
Tseng, Dissertation Abstracts Int. B., vol. 40, p. 3752, (1980).
Bernetti et al., J. Org. Chem., vol. 27, pp. 2863–2865, (1962).
Hurlbert et al., J. Med. Chem., vol. 11, pp. 708–710, (1968).
Arnold et al., Coll. Czech. Chem. Comm., vol. 25, pp. 1318–1323, (1980).
Arnold, Coll. Czech. Chem. Comm., vol. 26, pp. 3051–3057, (1961).
Stark et al., Tetrahedron, vol. 29, pp. 2209–2217, (1973).
Elslager et al., "Lectures in Heterocyclic Chemistry", vol. 2, pp. S-97, S-119–S-121, (1974).
Jones et al., European J. Cancer, vol. 17, pp. 11–19, (1981).
Rizkalla et al., J. Org. Chem., vol. 37, No. 25, pp. 3980–3985, (1972).
Grivsky et al., J. Med. Chem., vol. 23, pp. 327–329, (1980).

Primary Examiner—Donald G. Daus
Assistant Examiner—Stephen M. Kapner
Attorney, Agent, or Firm—Roylance, Abrams, Berdo & Goodman

[57] ABSTRACT

There are disclosed novel intermediates useful in the preparation of pyrido[2,3-d]pyrimidines having the following structures:

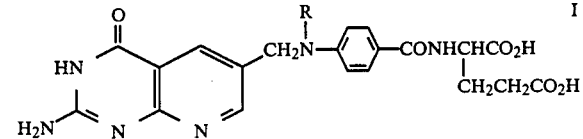

wherein R is CH$_3$, CH$_3$CH$_2$, CH$_3$CH$_2$CH$_2$, CH$_2$=CHCH$_2$ or CH≡CCH$_2$; and

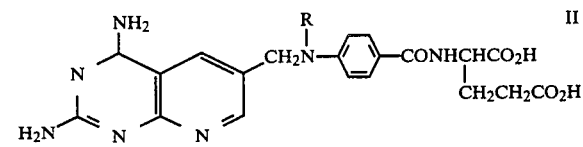

wherein R is CH$_3$, CH$_3$CH$_2$, CH$_3$CH$_2$CH$_2$, CH$_2$=CHCH$_2$ or CH≡CCH$_2$. These intermediates have the formulas:

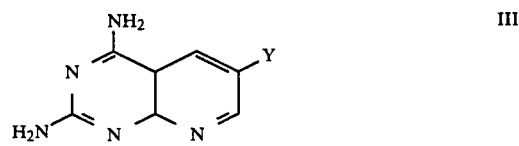

(Abstract continued on next page.)

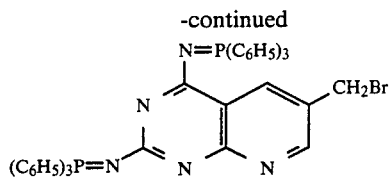 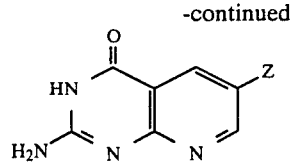
wherein Y is CHO, $CH_2OH$ or $CH_2Br$; and Z is $CH_2OH$ or $CH_2Br$.
1 Claim, No Drawings

PYRIDO(2,3-D)PYRIMIDINES

This is a division of application Ser. No. 673,283 filed Nov. 20, 1984, U.S. Pat. No. 4,536,575, which is a division of application Ser. No. 413,501, filed Aug. 31, 1982, U.S. Pat. No. 4,526,964, which is a continuation-in-part of application Ser. No. 338,542, filed Jan. 11, 1982, now U.S. Pat. No. 4,431,805; which is a continuation-in-part of application Ser. No. 305,907, filed Sept. 25, 1981, now abandoned.

BACKGROUND OF THE INVENTION

This invention relates to intermediates useful in the preparation of pyrido[2,3-]pyrimidines, which includes N-[4-[(2-amino-4(3H)-oxopyrido[2,3-d]-pyrimidin-6-yl)methylamino]benzoyl]-L-glutamic acid (5-deazafolic acid), N-[4[[(2-amino-4(3H)-oxopyrido[2,3-d]-pyrimidin-6-yl)methyl]methylamino]benzoyl]-L-glutamic acid (5-deaza-N$^{10}$-methylfolic acid), N-[4-[(2,4-,4-diaminopyrido[2,3-d]pyrimidin-6-yl)methylamino]benzoyl]-L-glutamic acid (5-deazaaminopterin), and N-[4-[[(2,4-diaminopyrido[2,3-d]pyrimidin-6-yl)methyl]methylamino]benzoyl]-L-glutamic acid (5-deazamethotrexate). This invention also relates to processes for using said intermediates; to the novel compounds 5-deaza-N$^{10}$-substituted aminopterin and 5-deaza-N$^{10}$-substituted folic acid; and to methods for preparing such novel compounds.

Powerful dihydrofolate reductase inhibitors such as aminopterin and methotrexate are known folic acid antagonists useful in the suppression and treatment of acute leukemia and related conditions. They have as their principal mechanism of action a competitive inhibition of the enzyme dihydrofolate reductase. Folic acid and its 7,8-dihydro derivative must be reduced to tetrahydrofolic acid by this enzyme in the process of DNA synthesis and cellular reproduction. Compounds having antifolate activity such as aminopterin and methotrexate inhibit the reduction of both folic acid and 7,8-dihydrofolic acid and interfere with tissue-cell reproduction.

Several types of quinazolinyl (5,8-dideazapteridinyl) analogs of folic acid, aminopterin, and methotrexate were reported to be inhibitors both of dihydrofolate reductase and thymidylate synthetase ([A. H. Calvert, T. R. Jones, P. J. Dady, B. Grzelakowska, R. M. Paine, G. A. Taylor and K. R. Harrap, *Europ. J. Cancer*, 16, 713 (1980); K. J. Scanlon, B. A. Moroson, J. R. Bertino and J. B. Hynes, *Mol. Pharmacol.*, 16, 261 (1979); O. D. Bird, J. W. Vaitkus and J. Clarke, *Mol. Pharmacol.*, 6, 573 (1970). Recently, N-[4-[N-[(2-amino-4-hydroxy-6-quinazolinyl)methyl]prop-2-ynylamino]benzoyl]-L-glutamic acid (5,8-dideaza-10-propargylfolic acid) was identified as a potent inhibitor of thymidylate synthetase [T. R. Jones, A. H. Calvert, A. L. Jackman, S. J. Brown, M. Jones and K. R. Harrap, *Europ. J. Cancer*, 17, 11 (1981)]. This enzyme catalyzes the de novo synthesis of thymidine nucleotides, which are required for DNA synthesis.

The synthesis of derivatives of the pyrido[2,3-d]pyrimidine ring system has been reviewed by W. J. Irwin and D. G. Wibberley, *Advan. Heterocycl. Chem.*, 10, 149 (1969), which covers the literature to the beginning of 1968. Although many methods are reported in this review, major routes to this ring system include the cyclization of the functional derivatives of 2-aminonicotinic acids with various reagents [e.g., R. K. Robins and G. H. Hitchings, *J. Am. Chem. Soc.*, 77, 2256 (1955)], and the reaction of derivatives of 4-aminopyrimidine with 1,3-dicarbonyl compounds or their masked derivatives [e.g., B. S. Hurlbert and B. F. Valenti, *J. Med. Chem.*, 11, 708 (1968)]. The condensations of 4-aminopyrimidines with malondialdehyde derivatives to give pyrido[2,3-d]pyrimidines are reported by R. Bernetti, F. Mancini and C. C. Price, *J. Org. Chem.*, 27, 2863 (1962), and B. S. Hurlbert and B. F. Valenti, *J. Med. Chem.*, 11, 708 (1968). A procedure for the preparation of 5-oxo-(8H)-pyrido[2,3-d]pyrimidines was reported by B. H. Rizkalla and A. D. Broom, *J. Org. Chem.*, 37, 3980 (1972). This reference discloses the following compound:

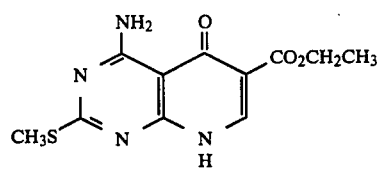

The development of procedures for the conversion of the above compound to N-[4-[(2,4-diamino-5-oxo(8H)-pyrido[2,3-d]pyrimidin-6-yl)methylamino]benzoyl]-L-glutamic acid (5-deaza-5-oxoaminopterin), i.e., a compound having the formula:

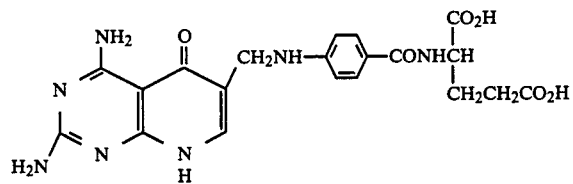

was reported by A. Srinivasan and A. D. Broom, *J. Org. Chem.*, 45, 3746 (1980). In addition, N-[4-[(2-amino-4(3H)-oxo-10-formylpyrido[2,3-d]pyrimidin-6-yl)methylamino]benzoyl]-L-glutamic acid (5-deaza-10-formylfolic acid), characterized only by spectral data, was reported to be formed from 5-deazafolate and formic acid by G. K. Smith, W. T. Mueller, P. A. Benkovic and S. J. Benkovic, *Biochemistry*, 20, 1241 (1981). A method for preparing 5-deazafolate is not disclosed.

The inhibition of bacterial dihydrofolate reductase by pryido[2,3-d]pyrimidines has been summarized in the *Advan. Heterocycl. Chem.* reference. Recently, a pyrido[2,3-d]pyrimidine derivative was reported to be a potent lipid-soluble inhibitor of mammalian dihydrofolate reductase by E. M. Grivsky, S. Lee, C. W. Sigel, D. S. Duch and C. A. Nichol, *J. Med. Chem.*, 23, 327 (1980). This reference discloses the compound:

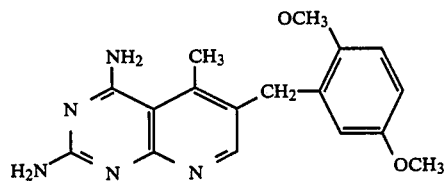

Other derivatives of this ring system have been evaluated for antihyptertensive activity. Thus, L. R. Bennett et al, *J. Med. Chem.*, 24, 382 (1981) reported that the following compound lowered blood pressure in the hypertensive rat:

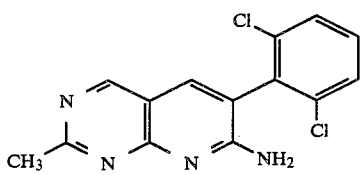

The synthesis of 5-deazafolic acid has been reported by D. T. Hurst, "An Introduction to the Chemistry and Biochemistry of Pyrimidines, Purines, and Pteridines", John Wiley and Sons, Ltd., 231 (1980). The synthesis of this compound using as an intermediate 2-amino-6-formyl-5-deazapteridine-4(3H-one), i.e., a compound having the formula:

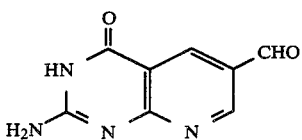

has been proposed by C. Temple, Jr. and J. A. Montgomery, "Synthesis of Potential Anticancer Agents", Cancer Chemotherapy National Service Center, Southern Research Institute, Progress Report 85, pages 1 and 2 (1966) and Progress Report 86, pages 8 and 10 (1967). The synthesis of 5-deazafolic acid via a condensation reaction involving triformylmethane has been reported by C. P. Tseng, Dissertation Abstracts Int. B, 40, 3752 (1980). The thesis upon which this abstract was based, C. P. Tseng, Studies in Heterocyclic Chemistry, 171–185 (1979) also describes unsuccessful work on the preparation of 5-deaza-2,4-diaminopteridine-6-carboxaldehyde dimethyl acetal, i.e., a compound having the formula:

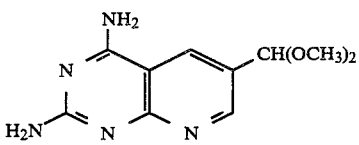

the synthesis of 5-deaza-6-formylpterin; and the conversion of this compound to 5-deazafolic acid via acetylated 5-deaza-6-formylpterin. The preparation of 5-deazaaminopterin via a long sequence of reactions involving the elaboration of a pyrimidine intermediate has been described by E. F. Elslager and J. Davoll, "Lectures in Heterocyclic Chemistry", 2, S-97, S-119–S-121 (1974).

SUMMARY OF THE INVENTION

The 5-deaza analogs of folic acid, $N^{10}$-substituted folic acid, aminopterin, $N^{10}$-substituted aminopterin and the diethyl ester of aminopterin inhibit the growth of human epidermoid carcinoma cells No. 2 and are active against leukemia in laboratory animals. The 5-deaza analogs of folic acid and $N^{10}$-substituted folic acid referred to herein have the following structure:

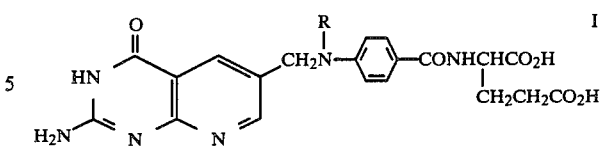

and the 5-deaza analogs of aminopterin and $N^{10}$-substituted aminopterin referred to herein have the following structure:

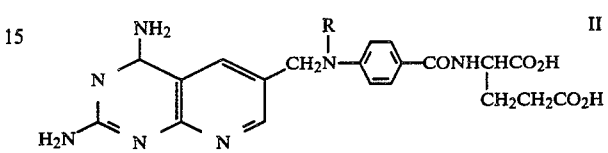

wherein R is hydrogen, $CH_3$, $CH_3CH_2$, $CH_3CH_2CH_2$, $CH_2{=}CHCH_2$, or $CH{\equiv}CCH_2$. Compounds of Formulas I and II wherein R is other than hydrogen are novel compounds.

Novel intermediates have now been found which are useful in the preparation of the compounds of Formulas I and II. These intermediates have the structures:

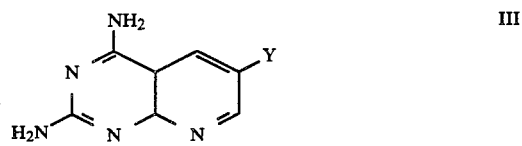

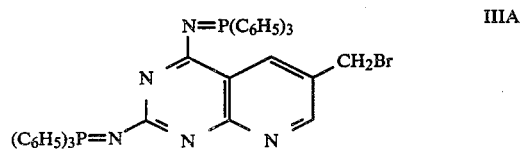

and

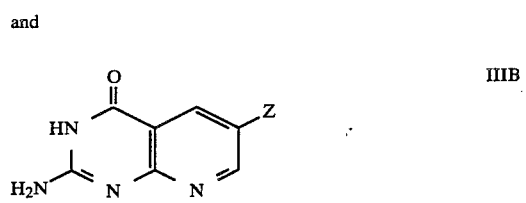

wherein Y is CHO, $CH_2OH$ or $CH_2Br$; and Z is $CH_2OH$ or $CH_2Br$.

Reductive alkylation and alkylation, respectively, of a dialkyl p-aminobenzoyl-L-glutamate having the structure:

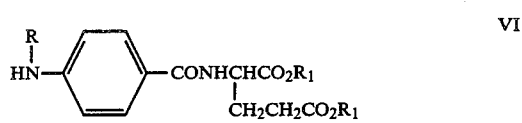

with the compounds of Formula III and Formula IIIA affords a compound having the structure:

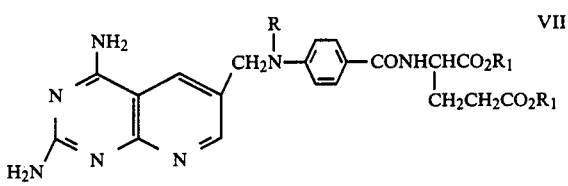

wherein R is the same as previously defined and $R_1$ is a lower alkyl group, i.e., a group containing up to six carbon atoms. Similarly, alkylation of a compound of Formula VI with a compound of Formula IIIB affords a compound having the structure:

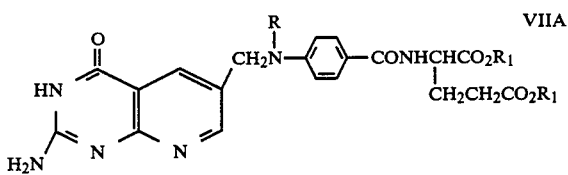

wherein R and $R_1$ are the same as previously defined. It is preferred when R in the compound of Formula VI is other than hydrogen, that the groups Y and Z on the compounds of Formulas III and IIIB be $CH_2Br$.

The compounds of Formula VII and VIIA can be converted to the compounds of Formulas II and I, respectively, by saponification. In addition, the compounds of Formula II can be treated under more drastic conditions with base to hydrolyze the 4-amino group according to the method described by R. Tratner, G. Elion, G. Hitchings, and D. Sharefkin, J. Org. Chem., 29, 2674 (1974) to give the compounds of Formula I. Also, the methylation of the compound of Formula II (R=H) with formaldehyde in the presence of sodium cyanoborohydride provides the compound of Formula II (R=$CH_3$). The compound of Formula I (R=$CH_3$) can also be prepared by methylation of the compound of Formula I (R=H) with the formaldehyde-sodium cyanoborohydride combination.

DETAILED DESCRIPTION OF THE INVENTION

The compound of Formula III (Y=CHO) is prepared by reaction of a compound having the structure:

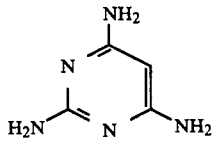

with the quaternary salt of triformylmethane (or its hydrolyzed derivatives) having the structure:

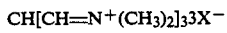

wherein X is a halogen atom, preferably chlorine.

The synthesis of triformylmethane was reported by Z. Arnold and J. Zemlicka, Coll. Czech. Chem. Commun., 25, 1318 (1960) and Z. Arnold, Coll. Czech. Chem. Commun., 26, 3051 (1961). Thus, in one method, reaction of bromoacetic acid with the complex $[(CH_3)_2N=CHCl]^+Cl^-$ resulting from treatment of N,N-dimethylformamide with phosphorus oxychloride gave a quaternary salt, probably V, which was treated with aqueous potassium carbonate to give triformylmethane. The isolation and purification of the latter is difficult, and in the procedure described herein, the intermediate quaternary salt or its hydrolyzed derivatives is used.

The condensation of V with 2,4,6-triaminopyrimidine (IV) in water at reflux gave 2,4-diaminopyrido[2,3-d]pyrimidine-6-carboxyaldehyde (III; Y=CHO). The structure of this compound was confirmed as described hereinafter in Example 8B by the alkaline potassium permanganate oxidation of the formyl group and hydrolysis of the 4-amino group to give the known 2-amino-4(3H)oxopyrido[2,3-d]pyrimidine-6-carboxylic acid (VIII) [R. Bernetti, F. Mancini and C. C. Price, J. Org. Chem., 27, 2863 (1962); D. M. Mulvery, S. G. Cottis and H. Tieckelmann, J. Org. Chem., 29, 2903 (1964)]. An authentic sample of VIII was prepared as described hereinafter in Example 8A by alkaline potassium permanganate oxidation of 2-amino-6-methyl-4(3H)oxopyrido[2,3-d]pyrimidine, which was synthesized by the method of E. Stark and E. Breitmaier, Tetrahedron, 29, 2209 (1973). It has been established that in the 2,4-diaminopyrido[2,3-d]pyrimidine ring system, the 4-amino function undergoes alkaline hydrolysis readily [R. Tratner, G. Elion, G. Hitchings, and D. Sharefkin, J. Org. Chem., 29, 2674 (1964)].

Although the mechanism of the condensation reaction is unknown, two of the formyl groups or potential formyl groups of V must react with the enamine moiety of the 4-aminopyrimidine with the elimination of either water or dimethylamine. The initial reaction involves the electrophilic attack of one formyl group or derivative either with the 5-position of the pyrimidine ring or with the 4-amino group to give a Schiff base followed by cyclization of the resulting monocyclic intermediate to give the desired bicyclic ring system. In the J. Org. Chem. reference above, Price et al observed that pyrido[2,3-d]pyrimidines were readily formed under mild conditions from 4-aminopyrimidines and malondialdehydes containing electron-withdrawing groups. Compound V can be considered a malondialdehyde derivative substituted with an electron-withdrawing group.

The compound of Formula III (Y=$CH_2OH$) is prepared by reducing the compound of Formula III (Y=CHO) in N,N-dimethylacetamide (DMAC) with sodium borohydride.

The compound of Formula III (Y=$CH_2Br$) is prepared by treating the compound of Formula III (Y=$CH_2OH$) with dibromotriphenylphosphorane in DMAC [procedure of J. R. Piper and J. A. Montgomery, J. Org. Chem., 42, 208 (1977)]. This results in the production of the corresponding 2,4-bis[(triphenylphosphoranylidene)amino] derivative, i.e., the compound of Formula IIIA. The compound of Formula IIIA can be converted to the compound of formula III (Y=$CH_2Br$) by the procedure described in the cited article by Piper and Montgomery. Either the compound of Formula IIIA or the compound of Formula III (Y=$CH_2Br$) can be used to react with a dialkyl p-aminobenzoyl-L-glutamate (VI); although it is preferred to use the compound of Formula IIIA, as illustrated in Example 3, Part B, which is formed in situ.

The compound of Formula IIIB (Z=$CH_2OH$), i.e., 2-amino-6-(hyroxymethyl)-4(3H)oxopyrido[2,3-d]pyrimidine, can be prepared by hydrolyzing the 4-amino group of the compound of Formula III (Y=$CH_2OH$) according to the method described in the earlier cited publication by R. Tratner, G. Elion, G. Hitchings and D. Sharefkin. Conversion of the compound of Formula IIIB ($Z=CH_2OH$) to 2-amino-6-(bromomethyl)-4-(3H)oxopyrido[2,3-d]pyrimidine (IIIB; $Z=CH_2Br$) is accomplished by treatment with phosphorus tribromide according to the procedure of S. Srinivasan and A. D. Broom, *J. Org. Chem.*, 46, 1777 (1981). In addition, the compound of Formula IIIB ($Z=CH_2Br$) can be prepared by hydrolysis of the 4-amino group of the compound of Formula III ($Y=CH_2Br$) with 48% hydrobromic acid according to the procedure of J. A. Montgomery, J. D. Rose, C. Temple, Jr. and J. R. Piper, "Chemistry and Biology of Pteridines", W. Pfleiderer, ed., Walter de Grugter, Berlin, 1976, p. 485.

The dialkyl p-(substituted amino)benzoyl-L-glutamates (VI) are prepared as described by A. H. Calvert, T. R. Jones, A. L. Jackman, S. J. Brown and K. R. Harrap, in "Advances in Tumour Prevention, Detection and Characterization, Vol. 5: Human Cancer. Its characterization and Treatment", W. Davis, K. R. Harrap and G. Stathopoulos, eds., Excerpta Medica, Amsterdam, 1980, P. 272; and T. R. Jones, A. H. Calvert, A. L. Jackman, S. J. Brown, M. Jones and K. R. Harrap, *Europ. J. Cancer*, 17, 11 (1981).

Reductive alkylation of diethyl p-aminobenzoyl-L-glutamate) (VI; $R=H$; $R_1=C_2H_5$) with III ($Y=CHO$) and hydrogen in 70% acetic acid containing Raney nickel gave a 32% yield of 5-deazaaminopterin diethyl ester. Saponification of the ester groups in a mixture of dimethyl sulfoxide-water at ambient temperature gave an 87% yield of 5-deazaaminopterin (II, $R=H$). Methylation of the latter compound was accomplished by treatment of II ($R=H$) with formaldehyde and sodium cyanoborohydride in aqueous solution at pH 6.4 to give an 85% yield of 5-deazamethotrexate (II, $R=CH_3$). The structure of II ($R=CH_3$) was established as described hereinafter in Example 8C by oxidation with alkaline potassium permanganate to give the previously prepared 2-amino-4(3H)oxopyrido[2,3-d]pyrimidine-6-carboxylic acid (VIII), which indicated that methylation had occurred either on the 4- or 10-amino group. Methylation of the 4-amino group was eliminated from consideration by alkaline hydrolysis of the 4-amino group to give 5-deaza-10-methylfolic acid (I, $R=CH_3$).

The preferred route for the preparation of I ($R=H$) involves the hydrolysis of 5-deazaaminopterin diethyl ester (VII; $R=H$; $R_1=C_2H_5$) in aqueous sodium hydroxide at reflux temperature, which resulted in replacement of the 4-amino group as well as hydrolysis of the ester functions to give a 79% yield of 5-deazafolic acid (I, $R=H$). Methylation of the compound of Formula I ($R=H$) with formaldehyde and sodium cyanoborohydride gave an 84% yield of 5-deaza-10-methylfolic acid (I, $R=CH_3$), which was identical to that prepared by the alkaline hydrolysis of the compound of Formula II ($R=CH_3$). The structures of I ($R=H$ and $CH_3$), II ($R=H$ and $CH_3$), and 5-deazaaminopterin diethyl ester were confirmed by elemental analysis, $^1$H-NMR and mass spectral data.

Reaction of the compound of Formula IIIB ($Z=CH_2Br$) with diethyl p-aminobenzoyl glutamate (VI; $R=H$; $R_1=C_2H_5$) gave N-[4-[(2-amino-4(3H)oxopyrido[2,3-d]pyrimidin-6-yl)methylamino]benzoyl]-L-glutamate (VIIA; $R=H$; $R_1=C_2H_5$), which was converted to a compound of Formula I ($R=H$) by saponification.

Compounds of Formulas I and II form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Therapeutic compositions containing compounds of Formulas I and II are useful for ameliorating cancer diseases in mammals. The active ingredients of the therapeutic compositions inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be adminstered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many case, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and (b) the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of adminstration of the said ingredients.

The following examples illustrate the best modes known for carrying out this invention:

EXAMPLE 1

2,4-Diamino-6-(carboxaldehyde)pyrido[2,3-d]pyrimidine (III; X=CHO).

Phosphorus oxychloride (27.5 ml, 46.0 g, 300 mmol) was added over 15 minutes with stirring to N,N-dimethylformamide (11.0 g, 150 mmol), which was cooled with an ice bath. After stirring at room temperature for 1 hour, the reaction mixture was treated with bromoacetic acid (13.9 g, 100 mmol). The resulting solution, protected by a calcium chloride tube was heated at 92° C. for 10 hours and evaporated to dryness in vacuo. The colored oil (~30 g) was dissolved in water (1000 ml), and the solution was neutralized with 50% sodium hydroxide to pH 7. After addition of 2,4,6-triaminopyrimidine (5.00 g, 40.0 mmol), the solution was refluxed for 3 hours and filtered hot through a fluted filter. The filtrate was cooled and the solid that precipitated was collected by filtration and dried in vacuo over $P_2O_5$: yield, 2.53 g (33%). Mass spectrum, m/e 189 (M+). HPLC [0.1M $NH_4OAc$ (pH 3.6)-$CH_3OH$ (9:1)] indicated that this product was 86% pure. A sample (200 mg) was dissolved in 0.1N HCl (15 ml) and diluted with acetone (225 ml) to precipitate impure III (Y=CHO): yield, 91 mg. The filtrate was evaporated to dryness under reduced pressure and the residue was dried in vacuo over $P_2O_5$ to give Compound III (Y=CHO): yield, 128 mg; mp, gradual darkening and decomposition with white subliminate when taken to 360° C. $\lambda_{max}$nm ($\epsilon$x $10^{-3}$): 0.1N HCl-258 (16.4), 317 (9.12), 326 sh (8.24); pH 7-263 (15.0), 316 (10.1), 345 (10.8); 0.1N NaOH-254 (13.2), 267 (13.5), 316 (8.56), 347 (10.0). $^1$H-

NMR (CF$_3$CO$_2$D, 6% w/v), 9.48 s, 9.75 s (5-CH, 7-CH), 10.21 s (6-CHO).

Anal. Calcd for C$_8$H$_7$N$_5$O.HCL.1.3H$_2$O: C, 38.57; H, 4.30; N, 28.12. Found: C, 38.44; H, 4.15; N, 28.14.

EXAMPLE 2

2,4-Diamino-6-(hydroxymethyl)pyrido[2,3-d]pyrimidine(III; Y=CH$_2$OH).

A solution of 2,4-diaminopyrido[2,3-d]pyrimidine-6-carboxaldehyde hydrochloride (200 mg, 0.884 mmol) in DMAC (40 ml) at 0° C. was treated with 1N NaOH (0.884 ml, 0.884 mmol) followed by a suspension of NaBH$_4$ (16.7 mg, 0.442 mmol) in DMAC (1 ml). The solution was stirred at 25° C. for 30 minutes and evaporated to dryness under high vacuum. A stirred suspension of the residue in H$_2$O (5 ml) was adjusted to pH 3 with 6N HCl, stirred for 5 minutes and adjusted to pH 7 with 1N NaOH. The precipitate was collected by filtration, washed with H$_2$O and dried in vacuo (P$_2$O$_5$); yield 121 mg (51%); mass spectrum, m/e 191 (M)$^+$, 87 (M)$^+$ for DMAC, 36 (M)$^+$ for HCl; $\lambda_{max}$nm ($\epsilon$x 10$^{-3}$): 0.1N HCl-274 (6.91), 318 (8.21), 330 sh (7.17), 362 (1.77); pH 7-248 (18.1), 271 (9.85), 338 (6.52); 0.1N NaOH-248 (19.7), 271 (10.3), 345 (7.14).

Anal. Calcd for C$_8$H$_9$N$_5$O.1.1HCl.0.4(CH$_3$)$_2$NCOCH$_3$: C, 43.32; H, 5.19; N, 28.42. Found: C, 43.48; H, 5.24; N, 28.48.

EXAMPLE 3

Diethyl N-[4-[(2,4-diaminopyrido[2,3-d]pyrimidine-6-yl)methylamino]benzoyl]-L-glutamate (VII); R=H; R$_1$=CH$_2$H$_5$).

A. A solution of Compound III (Y=CHO) (1.47 g, 5.90 mmol) in warm 70% acetic acid (59 ml) was cooled to 25° C., treated with diethyl p-aminobenzoyl-L-glutamate (2.28 g, 7.08 mmol) and hydrogenated in the presence of Raney nickel (6.3 g, weighed wet) at 25° C. and atmospheric pressure for 17 hours. The mixture was filtered and the catalyst was washed with 70% acetic acid (25 ml). The combined filtrates and wash was evaporated to dryness under high vacuum, and a solution of the residue in ethanol was filtered into 2N Na$_2$CO$_3$ (60 ml). The mixture was stirred to give a homogeneous powder which was collected, washed with water and dried. A solution of the resultant powder in boiling ethanol (415 ml) was filtered hot and evaporated to dryness in vacuo. The residue was triturated with CHCl$_3$ (85 ml), collected by filtration and the solid was washed with additional CHCl$_3$ (40 ml). A suspension of the solid in boiling ethanol (140 ml) was stirred for 20 minutes and refrigerated. The product was collected by filtration and dried in vacuo (P$_2$O$_5$): yield 945 mg (32%), mp 262° C. (Kofler Heizbank). Mass spectrum, m/e 496 (M+1)$^+$; $\lambda_{max}$nm ($\epsilon$x 10$^{-3}$): 0.1N HCl-218 (42.4), 280 sh (19.3), 300 (22.0); pH 7-218 (36.4), 249 (20.2), 280 sh (22.3) 297 (23.6), 355 sh (6.10); 0.1N NaOH-249 (22.0), 280 (23.8), 297 sh (22.5), 345 (7.23). $^1$H-NMR(DMSO-d$_6$6% w/v), $\delta$1.18 m CH$_3$, 2.05 m (CH$_2$CH$_2$CO), 2.43 t (CH$_2$CO), 4.08 m (CH$_2$O), 4.32 m (CH$_2$N, CHN), 6.31 s, 7.51 s (NH$_2$), 6.67 d, 7.69 d (C$_6$H$_4$), 6.71 s (CH$_2$NH), 8.25 d (CONH), 8.41 d (5-CH, J=2.0 Hz), 8.66 d (7-CH, J=2.0 Hz).

Anal. Calcd for C$_{24}$H$_{29}$N$_7$O$_5$: C, 58.17; H, 5.90; N, 19.79. Found: C, 57.91; H, 6.24; N, 19.55.

Evaporation of the filtrate and trituration of the residue with ethanol gave an additional 123 mg of less pure product, mp 246° C.

B. A solution of triphenylphosphine (430 mg, 1.64 mmol) in anhydrous DMAC (4 ml) at 0° C. was treated dropwise under N$_2$ with bromine (84 μL, 1.64 mmol). The solution was stirred at 0° C. for 15 minutes, treated with the compound obtained in Example 2 (100 mg, 0.38 mmol), and stirred at 25° C. for 1.7 hours to give the compound of Formula IIIA. This solution was treated with diethyl p-aminobenzoyl-L-glutamate (194 mg, 0.603 mmol), stirred at 25° C. for 17 hours and poured into ice water (40 ml). The resulting solution (pH 2) was filtered to remove triphenylphosphine oxide, adjusted to pH 6.8 with 50% NaOH, and cooled in an ice bath. The precipitate of crude product (VII; R=H, R$_1$=C$_2$H$_5$) was collected by centrifugation, washed with H$_2$O and dried in vacuo (P$_2$O$_5$); yield 136 mg (73%). The retention time (HPLC) and rf value (TLC) of this product were identical to those obtained from the analytical sample obtained in Part A of this example. Mass spectrum: m/e 496 (M+1)$^+$.

EXAMPLE 4

N-[4-[(2-Amino-4(3H)-oxopyrido[2,3-d]pyrimidin-6-yl)methylamino]benzoyl]-L-glutamic Acid (I, R=H).

A suspension of the product obtained in the previous example, VII (R=H, R$_1$=C$_2$H$_5$) (100 mg, 0.202 mmol) in O$_2$ free 1N NaOH (4 ml) was stirred at reflux temperature under N$_2$ for 4.25 hours and acidified to pH 3.1 with 6N HCl. The precipitate was collected by filtration and dried in vacuo. A solution of the solid in 1N HCl (0.5 ml) was diluted with water (0.5 ml), filtered, diluted with water (9 ml) and adjusted to pH 3.1 with 1N NaOH. The precipitate was collected by filtration, washed with water at pH 3.1 and dried in vacuo (P$_2$O$_5$): yield 74 mg (79%), mp indefinite; mass spectrum, m/e 441 (M+1)$^+$; $\lambda_{max}$nm ($\epsilon$x 10$^{-3}$): 0.1N HCl-213 (37.0), 280 (23.9), 297 sh (20.6), 350 (7.35); pH 7-216 (40.8), 278 (24.9), 295 sh (23.8); 0.1N NaOH-243 (22.9), 278 (24.0), 295 sh (22.7), 345 sh (7.58); $^1$H-NMR (CF$_3$CO$_2$D, <6% w/v), 2.56 (CH$_2$CH$_2$CO), 2.82 t (CH$_2$O), 5.11 m (CHN, CH$_2$N), 7.87 d, 8.15 d (C$_6$H$_5$), 8.98 s, 9.10 s (5-CH, 7-CH).

Anal. Calcd for C$_{20}$H$_{20}$N$_6$O$_6$.1.1H$_2$O: C, 52.20; H, 4.86; N, 18.26. Found: C, 52.00; H, 4.92; N, 18.54.

EXAMPLE 5

N-[4-[(2,4-Diaminopyrido[2,3-d]pyrimidine-6-yl)methylamino]benzoyl]-L-glutamic acid (II, R=H).

A solution of the product obtained in Example 3, VII (R=H, R$_1$=C$_2$H$_5$) (359 mg, 0.724 mmol) in dimethyl sulfoxide (10 ml) under N$_2$ was treated with 1N NaOH (1.81 ml, 1.81 mmol), stirred in a stoppered flask under N$_2$ for 6 hours, and evaporated to dryness in vacuo at <30° C. A solution of the residue in water (18 ml) was filtered and acidified to pH 3.6 with 1N HCl. The precipitate was collected by filtration, washed with water at pH 3.6 and dried in vacuo (P$_2$O$_5$); yield 297 mg (87%), mp indefinite (softens above 200° C.); mass spectrum, m/e 440 (M+1)$^+$; $\lambda_{max}$nm ($\epsilon$x 10$^{-3}$): 0.1N HCl-218 (40.5), 280 sh (16.9), 300 (18.8); pH 7-218 (38.5), 245 (19.2), 280 (23.9), 296 sh (22.7); 0.1N NaOH-248 (22.0), 280 (24.4), 296 sh (22.7), 345 (7.75); $^1$H-NMR (DMSO-d$_6$, 6% w/v), $\delta$2.00 m (CH$_2$CH$_2$CO), 2.29 t (CH$_2$CO), 4.36 m (CHN, CH$_2$N), 6.66 d, 7.68 d (C$_6$H$_4$), 7.41

($NH_2$), 8.04 m ($NH_2$, NH, $CO_2H$), 8.52 d, 8.70 d (5-CH, 7-CH).

Anal. Calcd. for $C_{20}H_{21}N_7O_5 \cdot 1.9H_2O$: C, 50.72; H, 5.28; N, 20.70. Found: C, 50.86; H, 5.43; N, 20.50.

EXAMPLE 6

N-[4-[[(2,4-Diaminopyrido[2,3-d]pyrimidine-6-yl)methyl]methylamino]benzoyl]-L-glutamic acid (II, R=$CH_3$).

A suspension of Compound II (R=H) (100 mg, 0.211 mmol) in $O_2$ free water (5 ml) under $N_2$ was adjusted to pH 6.4 with 1N NaOH to give a solution which was treated with 38% HCHO (83.1 μl, 1.14 mmol) followed by $NaBH_3CN$ (19.9 mg, 0.317 mmol). The solution was maintained at pH 6.4 by gradual addition of 1N HCl over a period of 45 minutes. The solution was stirred under $N_2$ for 23 hours, filtered and acidified to pH 3.6 with 1N HCl. The product was collected by filtration, washed with water at pH 3.6 and dried in vacuo ($P_2O_5$): yield 97 mg (94%, mp indefinite (softens and darkens above 217° C.); mass spectrum, m/e 454 (M+1)+; $\lambda_{max}$nm (ex $10^{-3}$): 0.1N HCl-221 (37.1), 311 (19.0); pH 7-219 (35.1), 247 (18.1), 305 (25.2); 0.1N NaOH-249 (19.9), 305 (25.0), 355 sh (6.15; $^1$H-NMR (DMSO-$d_6$, <5% w/v), δ2.00 m ($CH_2CH_2CO$), 2.28 t ($CH_2CO$), 3.12 s ($CH_3$), 4.32 m (CHN), 4.66 s ($CH_2N$), 6.78 d, 7.72 d ($C_6H_4$), 8.31 d (5-CH), 8.59 d (7-CH).

Anal. Calcd. for $C_{21}H_{23}N_9O_5 \cdot 2H_2O$: C, 51.53; H, 5.56; N, 20.03. Found: C, 51.54; H, 5.47; N, 20.35.

EXAMPLE 7

N-[4-[[(2-Amino-4(3H)-oxopyrido[2,3-d]pyrimidine-6-yl)methylamino]benzoyl]-L-glutamic acid (I, R=$CH_3$).

A. A suspension of I (R=H) (60 mg, 0.13 mmol) was methylated by the procedure used for the preparation of II (R=$CH_3$). The reaction solution after filtration was diluted with oxygen free water (3 ml) and acidified to pH 3.1 with 1N HCl. The product was collected, washed with water at pH 3.1 and dried in vacuo ($P_2O_5$); yield 53 mg (84%), mp indefinite; mass spectrum, m/e 455 (M+1)+; $\lambda_{max}$nm (ex$10^{-3}$): 0.1N HCl-215 (35.1), 280 (19.0), 306 (20.8), 355 sh (6.85); pH 7-216 (38.0), 274 (19.0), 306 (27.3); 0.1N NaOH-242 (22.9), 275 sh (17.4), 307 (25.4); $^1$H-NMR (DMSO-$d_6$, 5% w/v), δ2.02 m ($CH_2CH_2CO_2H$), 2.35 t ($CH_2CO$), 3.09 s ($CH_3$), 4.37 m (CHN), 4.73 s ($CH_2N$), 6.82 d, 7.75 d ($C_6H_4$), 8.03 d (5-CH), 8.19 d (NH), 8.55 d (7-CH).

Anal. Calcd. for $C_{21}H_{22}N_6O_5 \cdot H_2O \cdot 0.75$ HCl: C, 52.14; H, 5.16; N, 17.3. Found: C, 52.12; H, 5.12; N, 17.47.

B. A solution of Compound II (R=$CH_3$) (50 mg) was hydrolyzed by the procedure of Example 4 for the preparation of Compound I (R=H) to give a 64% yield of Compound I (R=$CH_3$). HPLC and uv data indicated that this product was identical to that prepared in A above.

EXAMPLE 8

2-Amino-4(3H)-oxopyrido[2,3-d]pyrimidine-6-carboxylic Acid (VIII).

A. To a solution of 2-amino-6-methyl-4(3H)oxopyrido[2,3-d]pyrimidine (177 mg, 1.00 mmol) in 1N NaOH (60 ml) at reflux temperature was added with stirring an aqueous solution of 0.2M potassium permanganate over a period of about 1 hour. After the excess permanganate was destroyed with sodium bisulfite, the resulting hot mixture was filtered through Celite. The filtrate was adjusted to ~pH 3 with HCl and allowed to stand at room temperature for 18 hours. The solid that precipitated (170 mg) was collected by filtration, dissolved in 2N NaOH, and the solution was cooled to deposit the sodium salt of the product. The salt was collected by filtration, dissolved in water, and the solution was adjusted to pH 2-3 with HCl. The solid that deposited was collected by filtration and dried in vacuo over $P_2O_5$: yield, 67 mg (29%); mp 265° C. HPLC [0.1M $Na_2HPO_4$ (pH 7)-$CH_3CN$ (92:8)] showed that this sample was homogeneous. $\lambda_{max}$nm (ex$10^{-3}$): 0.1N HCl-216 (35.9), 266 (14.5), 306 (6.70), 315 sh (5.35); pH 7-216 (26.8), 232 sh (17.8), 283 (11.4), 310 sh (5.93), 321 sh (5.37); 0.1N NaOH-246 (22.8), 292 (10.1), 332 (7.20). $^1$H-NMR (NaOD, 5% w/v), δ8.76 d (7-CH, J=1.5 Hz), 9.06 d (5-CH).

Anal. Calcd for $C_8H_6N_4O_3 \cdot 0.6$ HCl: C, 42.13; H, 2.92; N, 24.57. Found: C, 42.04; H, 2.80; N, 24.41.

B. Treatment of 2,4-diaminopyrido[2,3-d]pyrimidine-6-carboxaldehyde (III; Y=CHO) (186 mg, ~0.980 mmol) by the procedure described in A resulted in hydrolysis of the 4-amino group and oxidation of the formyl group to give VIII: yield, 158 mg; Field desorption mass spectrum, m/e 206 (M+). The HPLC chromatogram (co-injection) of this product was identical with that of Compound VIII prepared in A.

C. A solution of N-[4-[[(2,4-diaminopyrido[2,3-d]pyrimidin-6-yl)methyl]methylamino]benzoyl]-L-glutamic acid (II, R=$CH_3$) (5.00 mg, 0.010 mmol) in 2 ml of 1N NaOH was treated with $KMnO_4$ (1.62 mg, 0.010 mmol), heated at 95° C. for 3 hours, filtered and adjusted to pH 8 with 1N HCl. An HPLC chromatogram indicated the presence of VIII (~22% yield) and unreacted II (R=$CH_3$) (~50% recovery). The ultraviolet spectrum (240-360 nm) of the eluted Compound VIII was identical to the ultraviolet spectrum of an authentic sample.

Cell culture cytotoxicity data and activity against lymphocytic leukemia P388 in mice for Compounds I, II and VII (R=H; $R_1$=$C_2H_5$) are set forth in Table 1.

TABLE 1

| Cell Culture Cytotoxicity Data[a] and Activity Against Lymphocytic Leukemia P388 in Mice[b] | | | |
|---|---|---|---|
| | | P388[d] | |
| Compound | $ED_{50}\mu M$[c] | dose, mg/kg | % ILS |
| I (R = H) | 6.1 | 100 | 17 |
| I (R = $CH_3$) | 11.2 | 200 | 11 |
| II (R = H) | 0.013 | — | — |
| II (R = $CH_3$) | 0.004 | 4 | 92[e] |
| VII (R = H; $R_1$ = $C_2H_5$) | 0.052 | 1 | 118 |
| Methotrexate | 0.001 | 2 | 61[f] |

[a]Human epidermoid carcinoma cell No. 2. R. I. Geran, N. H. Greenberg, M. M. MacDonald, A. M. Schumacher, and B. J. Abbott, Cancer Chemotherapy Reports, Part 3, Vol. 3 (No. 2), 1971.
[b]Reference in a.
[c]Concentrations inhibiting colony formation by 50% after 12 days as determined in plastic flask. L. L. Bennett, Jr., H. D. Schnetti, N. H. Vail, P. W. Allan, and J. A. Montgomery, Mol. Pharmacol., 2, 432 (1966).
[d]$CDF_1$ mice inoculated with $10^6$ P388 cells intraperitoneally; drug administered intraperitoneally on qd 1-5 days.
[e]One 30th-day survivor.
[f]Administered intraperitoneally on qd 1-9 days.

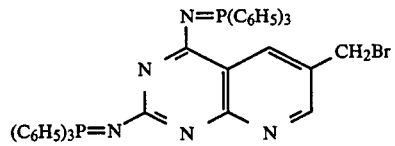

What is claimed is:

1. A dimethylacetamide solution of a compound having the structure: